United States Patent [19]

Mrowca

[11] Patent Number: 4,668,806

[45] Date of Patent: May 26, 1987

[54] PROCESS FOR PREPARING METHYLCARBAMATE INSECTICIDES

[75] Inventor: Joseph J. Mrowca, Wilmington, Del.

[73] Assignee: E. I. Du Pont de Nemours and Company, Wilmington, Del.

[21] Appl. No.: 724,769

[22] Filed: Apr. 18, 1985

[51] Int. Cl.$^4$ .......................................... C07D 307/86
[52] U.S. Cl. ...................................... 549/470; 558/3; 560/134; 564/255
[58] Field of Search .................... 549/470; 560/134; 564/255; 260/453.3, 453 P; 558/3

[56] References Cited

U.S. PATENT DOCUMENTS 4,495,107 1/1985 Dodge et al. .................. 260/453 P Primary Examiner—John M. Ford
Assistant Examiner—Bernard I. Dentz

[57] ABSTRACT

Reacting an alkali metal cyanate salt with dimethyl sulfate in acetonitrile, heating in a steady stream of nitrogen and thereafter immediately bubbling the formed methyl isocyanate into a solution of an appropriate oxime or phenol to form an N-methylcarbamate.

5 Claims, No Drawings

PROCESS FOR PREPARING METHYLCARBAMATE INSECTICIDES

BACKGROUND OF THE INVENTION

This invention relates to a process for making insecticidal compounds. More particularly, it refers to an improved process for making N-methylcarbamates.

The following patents describe methods of making N-methylcarbamate insecticides or the methyl isocyanate intermediate for making N-methylcarbamates.

1. U.S. Pat. No. 3,576,834 discloses a method for the preparation of methomyl insecticide as shown below.

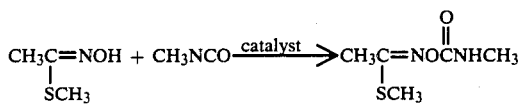

2. U.S. Pat. No. 3,658,870 teaches a similar method for the preparation of oxamyl insecticide.
3. U.S. Pat. No. 3,217,037 describes insecticides such as aldicarb.
4. U.S. Pat. Nos. 3,474,170 and 3,474,171 describe carbofuran as an insecticide.
5. U.S. Pat. No. 2,903,478 describes novel insecticides such as carbaryl.
6. U.S. Pat. No. 4,255,350 describes a method for preparing methyl isocyanate wherein a mixture of potassium cyanate, potassium iodide and DMF in m-xylene is treated with methyl chloride at 120° C.
7. U.S. Pat. No. 4,206,136 teaches the preparation of methyl isocyanate by treatment of potassium cyanate with dimethyl sulfate in the presence of calcium oxide and/or calcium chloride in a refluxing solvent such as dichlorobenzene.

Several methods, in addition to those set forth in the aforementioned references, are known in the art for the preparation of N-methylcarbamates. Perhaps the most widely-known procedure involves treatment of the appropriate starting material, ROH, as hereafter identified with methyl isocyanate. This process suffers from the disadvantage of requiring the handling and storage of methyl isocyanate, which is both burdensome and extremely hazardous, as well as being comparatively expensive on an industrial scale.

Methyl isocyanate can be synthesized in several ways including the two procedures taught in references 6 and 7 above or thirdly, the reaction of phosgene with monomethylamine.

The first and second processes suffer several drawbacks including the need for high reaction temperatures, expensive and/or toxic cosolvents (DMF is a known embryotoxin), gaseous reactants (methyl chloride), and additives such as potassium iodide, calcium oxide or calcium chloride.

The third process suffers from several disadvantages. First, both phosgene and monomethylamine are gases at ambient temperature, and phosgene is extremely toxic. Second, this reaction evolves two moles of hydrogen chloride for each mole of reactant consumed; disposal of this strongly acidic and corrosive by-product can be costly.

The most serious prior art problem occurs when large quantities of methyl isocyanate must be isolated and transported for long distances, before conversion into the N-methylcarbamate insecticide. The extreme toxicity of methyl isocyanate is now well known throughout the world. A process needed to be developed which produced N-methylcarbamates at low cost without the necessity of isolating methyl isocyanate during the processing steps.

SUMMARY OF THE INVENTION

The instant invention offers a convenient, mild, and highly efficient process for the controlled production of methyl isocyanate, closely coupled with a means for its immediate consumption. Such a process is highly desirable as it produces well-known pesticides without the need for the handling and storage of large quantities of methyl isocyanate.

The process for the preparation of N-methylcarbamates of Formula I is carried out as shown in Equation 1.

EQUATION 1

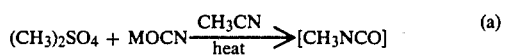

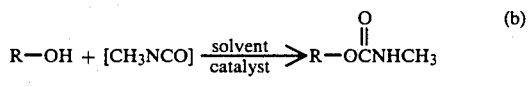

wherein
M is potassium or sodium; and
R is of the formula

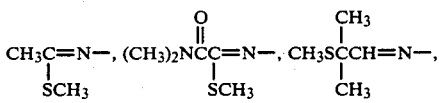

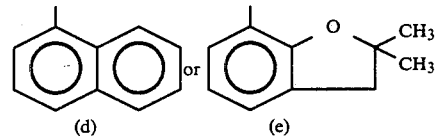

The compounds of Formulae I (a)–I(e) are very useful in controlling insects and other arthropod pests. These pesticides are known commercially as methomyl, oxamyl, aldicarb, carbaryl and carbofuran, respectively.

In Equation 1(a), a mixture of an alkali metal cyanate salt and dimethyl sulfate in acetonitrile solvent is heated under a steady stream of nitrogen. Other process parameters include:

|  | GENERAL | PREFERRED |
|---|---|---|
| Cyanate Salt | potassium or sodium cyanate | potassium cyanate |
| Temperature | 40°–85° C. | 60°–85° C. |
| Reaction Time | 1–24 hours | 6–8 hours |
| Equivalents of Cyanate Salt | at least one (based on dimethyl sulfate) | one (based on dimethyl sulfate) |

In Equation 1(b), the nitrogen effluent from step (a) carrying methyl isocyanate is bubbled into a stirred mixture of the appropriate oxime or phenol of Formula II at room temperature.

Other parameters include:

|  | GENERAL | PREFERRED |
| --- | --- | --- |
| Solvent | methylene chloride, water, cyclohexanone methyl isobutyl ketone | methylene chloride when the oxime is II(a): water when the oxime is II(b). |
| Reaction Time | 1–24 hours | 6–8 hours |
| Catalyst | triethylamine, pyridine, dimethyl-amino pyridine, dibutyltin dilaurate | triethylamine |
| Equivalents of Oxime or Phenol (II) | less than one (based on dimethyl sulfate) | 0.67–0.95 (based on dimethyl sulfate) |

These two reactions are generally carried out in a closely coupled process at atmospheric pressure. As the methyl isocyanate forms in step (a), it is passed into the solution of oxime or phenol of Formula II via nitrogen stream. The desired product of Formula I can be isolated by conventional procedures, such as extraction with a suitable organic solvent or simple evaporation of the reaction solvent.

DETAILED DESCRIPTION OF THE INVENTION

This invention provides an improved process for preparing N-methylcarbamates of Formula I by heating potassium or sodium cyanate with dimethyl sulfate in acetonitrile, and passing the evolved methyl isocyanate in a nitrogen stream into a mixture of an appropriate oxime or phenol of Formula II in an inert solvent, optionally in the presence of a catalyst.

The starting compounds of Formula II are known in the art and have been taught as intermediates for the production, by other processes, of the above-mentioned N-methylcarbamate insecticides.

In the conduct of Equation 1(a), potassium or sodium cyanate is reacted with dimethyl sulfate in acetonitrile under a nitrogen stream. The temperature of the reaction is maintained at 40°–85° (reflux), preferably between 60° and 85° (reflux). The reaction time depends on such factors as the reaction temperature and reactant concentrations, but generally will range from 1–24 hours, preferably between 6–8 hours. At least one equivalent of cyanate salt (based on dimethyl sulfate) is used with one equivalent (based on dimethyl sulfate) being preferred.

The nitrogen effluent from Equation 1(a) carrying methyl isocyanate is passed through a condenser to condense acetonitrile solvent, and is bubbled into a stirred mixture of the appropriate oxime or phenol of Formula II in an inert solvent at room temperature (Equation 1(b)). Suitable solvents for Equation 1(b) are methylene chloride, water, cyclohexanone, or acetone with methylene chloride preferred when the oxime is II(b), and water when the oxime is II(a). An optional catalyst can be used to accelerate Equation 1(b), and this can be selected from triethylamine, pyridine, 4-dimethylaminopyridine, dibutyltin dilaurate, or 1,4-diazabicyclo[2.2.2]octane with triethylamine as a preferred catalyst, especially with methylene chloride as solvent. Generally, in Equation 1(b), less than one equivalent of oxime or phenol (II) (based on dimethyl sulfate) is used with 0.67–0.95 equivalents of oxime or phenol (II) (based on dimethyl sulfate) preferred. The two reactions, set forth in Equations 1(a) and 1(b), are generally carried out in a closely-coupled process at atmospheric pressure so that the times of both reactions are about equal.

The desired product of Formula I can be used as prepared in solution or isolated by conventional procedures, such as extraction with a suitable organic solvent or simple evaporation of the reaction solvent.

This invention is further illustrated by the following five examples, wherein temperatures are given in degrees Celsius unless otherwise indicated.

EXAMPLE 1

A mixture of 6.08 g of potassium cyanate, 9.45 g of dimethyl sulfate, and 40 ml of acetonitrile was gently refluxed in a nitrogen stream. The stream was passed through a condenser and bubbled into a stirred mixture of 8.10 g of methyl-2-(dimethylamino)-N-hydroxy-2-oxoethanimidothioate in 40 ml of methylene chloride containing two drops of triethylamine for 7.25 hours. The resulting solution was evaporated to give 11.0 g of a white solid, m.p.107°–108°, containing 97.4% of methyl N',N'-dimethyl-N-[(methylcarbamoyl)-oxy]-1-thiooxamimidate (oxamyl).

EXAMPLE 2

The procedure of Example 1 was followed, using 4.46 g of potassium cyanate and 6.94 g of dimethyl sulfate to yield 10.4 g of a white solid, m.p. 99°–102°, containing 88% of oxamyl.

EXAMPLE 3

The procedure of Example 1 was followed, substituting 4.88 g of sodium cyanate for the potassium cyanate to afford 7.93 g of a white solid containing 20.3% oxamyl and 79.6% of the starting imidothioate.

EXAMPLE 4

The procedure of Example 1 was followed, substituting 7.21 g of 1-naphthol for the imidothioate to yield 10.7 g of tan solid, m.p. 137°–140°, containing 92% of 1-napthyl N-methylcarbamate (carbaryl).

EXAMPLE 5

A mixture of 6.08 g of potassium cyanate, 9.45 g of dimethyl sulfate, and 40 ml of acetonitrile was gently refluxed in a nitrogen stream. The stream was passed though a condenser and bubbled into a stirred mixture of 5.25 g of methyl N-hydroxythioacetimidate in 40 ml of water for 7 hours. The resulting water solution weighed 47.2 g and contained 15.8% of methyl-N-{[(methylamino)carbonyl]oxy}ethanimidothioate (methomyl).

What is claimed is:

1. In a process for preparing N-methylcarbamates by (a) reacting an alkali metal cyanate with dimethyl sulfate to form methyl isocyanate and (b) reacting said methyl isocyanate with ROH to form a compound of the formula

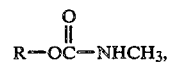

wherein R is selected from the formulae

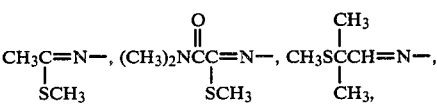

-continued

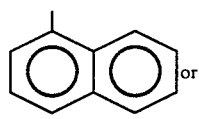 or

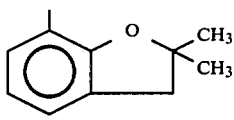

the improvement which comprises operating step (a) in acetonitrile solvent and immediately bubbling the methyl isocyanate from step (a) into the ROH of step (b).

2. A process according to claim 1 wherein the alkali metal cyanate salt is potassium cyanate.

3. A process according to claim 1 wherein the alkali metal cyanate salt is sodium cyanate.

4. A process according to claim 2 wherein the reaction temperature in step (a) is 60°–85° C. and triethylamine is used as a catalyst in step (b).

5. A process according to claim 3 wherein the reaction temperature in step (a) is 60°–85° C. and triethylamine is used as a catalyst in step (b).

* * * * *